United States Patent [19]
Serbousek et al.

[11] Patent Number: 5,336,265
[45] Date of Patent: Aug. 9, 1994

[54] REDUCED STIFFNESS FEMORAL HIP IMPLANT

[75] Inventors: Jon Serbousek, Warsaw; Alexandre DiNello, Ft. Wayne, both of Ind.

[73] Assignee: De Puy, Inc., Warsaw, Ind.

[21] Appl. No.: 975,993

[22] Filed: Nov. 13, 1992

Related U.S. Application Data

[63] Continuation of Ser. No. 773,027, Oct. 7, 1991, abandoned.

[51] Int. Cl.$^5$ .............................................. A61F 2/30
[52] U.S. Cl. ........................................ 623/18; 623/23
[58] Field of Search ................... 623/16, 18, 22, 23

[56] References Cited

U.S. PATENT DOCUMENTS

| Re. 28,895 | 7/1976 | Noiles | 3/1.912 |
|---|---|---|---|
| Re. 32,488 | 9/1987 | Gustilo et al. | 623/23 |
| 2,627,855 | 2/1953 | Price | 128/92 |
| 3,623,164 | 11/1971 | Bokros | 128/92 |
| 3,740,769 | 6/1973 | Haboush | 3/1 |
| 3,893,196 | 7/1975 | Hochman | 3/1.91 |
| 3,965,490 | 6/1976 | Murray et al. | 3/1.913 |
| 3,995,323 | 12/1976 | Shersher | 3/1.913 |
| 4,164,794 | 9/1979 | Spector et al. | 623/18 |
| 4,261,063 | 4/1981 | Blanquaert | 3/1.91 |
| 4,404,693 | 9/1983 | Zweymuller | 3/1.913 |
| 4,475,545 | 10/1984 | Ender | 128/92 |
| 4,535,487 | 8/1985 | Esper et al. | 623/22 |
| 4,536,894 | 8/1985 | Galante et al. | 623/22 |
| 4,546,501 | 10/1985 | Gustilo et al. | 623/23 |
| 4,623,349 | 11/1986 | Lord | 623/18 |
| 4,661,112 | 4/1987 | Muller | 623/22 |
| 4,714,470 | 12/1987 | Webb, Jr. et al. | 623/18 |
| 4,808,186 | 2/1989 | Smith | 623/22 |
| 4,921,501 | 5/1990 | Giacometti | 623/23 |
| 4,986,834 | 1/1991 | Smith et al. | 623/18 |
| 5,002,578 | 3/1991 | Luman | 623/23 |
| 5,002,581 | 3/1991 | Paxson et al. | 623/18 |
| 5,007,931 | 4/1991 | Smith | 623/23 |
| 5,018,285 | 5/1991 | Zolman et al. | 623/23 |
| 5,035,718 | 7/1991 | Berchem | 623/18 |

OTHER PUBLICATIONS

J. Engelhardt et al., "Effect of Femoral Component Section Modulus on the Stress Distribution in the Proximal Human Femur" *Med. & Biol. Eng. & Comput.* 26, (1988) Jan., No. 1, pp. 38–45.

"Cementless Fixation of 'Isoelastic' Hip Endoprostheses Manufactured from Plastic Materials", E. W. Morscher, M.D. et al. *Clinical Orthopaedics* Jun., 1983, pp. 77–87.

"The Importance of Stem Geometry, Porous Coating, and Collar Angle of Femoral Hip Prostheses on the Stress Distribution in the Human Femur", J. P. Collier, et al, 9th Annual Meeting of the Society for Biomaterials, Birmingham, Alabama, Apr. 27–May 1, 1983, p. 96.

*Primary Examiner*—David Isabella
*Attorney, Agent, or Firm*—Perman & Green

[57] ABSTRACT

A femoral component of an artificial hip joint includes an elongated stem with a single longitudinally extending, medially facing, groove in its outer surface intermediate its proximal and distal ends. The dimensions of the groove are chosen so as to obtain constant stiffness or, alternatively, a predetermined stiffness of the stem between the proximal and distal ends. In either event, the stem has a magnitude of stiffness no greater than that at which stress shielding of the first bone would occur. The groove and the outer surface of the stem intersect at an outer rim. The groove has a central concave surface and proximal and distal radiused end surfaces in communication with and blending smoothly with the central cylindrical concave surface. The groove is disposed at an angle within a range of 0° to approximately 45° relative to the coronal plane, extending in a lateral posterior to medial anterior direction. The component is preferably composed of titanium, titanium alloy, or cobalt-chromium alloy. The outer surface of the stem may be provided with a porous medium for encouraging bone ingrowth fixation.

9 Claims, 3 Drawing Sheets

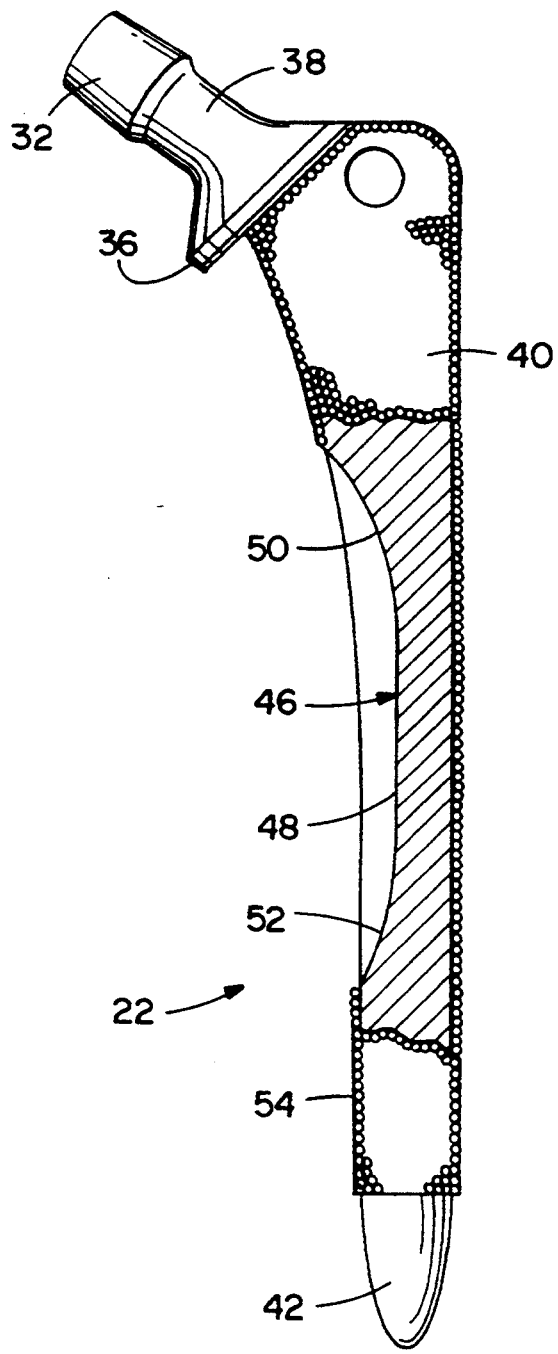
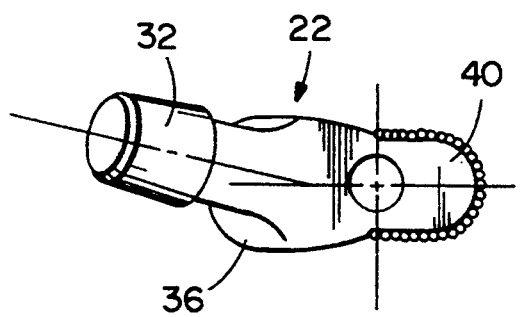
FIG. 3
FIG. 4

×—UNMODIFIED STEM
•—MODIFIED (CONSTANT MOMENT) STEM
×—MODIFIED (VARIABLE MOMENT) STEM

☐ UNMODIFIED STEM

▨ MODIFIED (CONSTANT MOMENT) STEM

▨ MODIFIED (VARIABLE MOMENT) STEM

REDUCED STIFFNESS FEMORAL HIP IMPLANT

This is a continuation of copending application Ser. No. 07/773,027, filed on Oct. 7, 1991, now abandoned.

BACKGROUND OF THE INVENTION

1. Field of the Invention

The present invention relates generally to a femoral hip prosthesis and, more particularly, to a femoral component having a stem which exhibits substantially controlled stiffness between its proximal and distal ends.

2. Description of the Prior Art

Based on the precepts of Wolff's Law which states that bone tissue will remodel in direct relation to the stress applied to it, it has previously been considered desirable to stress bone at an optimal level to minimize and control remodeling after THR (total hip replacement) arthroplasty. Usually some degree of proximal femur bone remodeling accompanies total hip replacement. Due to mechanical stiffness, metallic implants typically stress protect the proximal bone to some extent. This phenomena is clinically referred to as "stress shielding". In patients with relatively large intramedullary canals which require a large diameter implant for optimal fit, this phenomenon of "stress shielding" may be particularly troublesome. In the most extreme case, the proximal femoral bone may resorb to a small fraction of its original mass, possibly causing a loss of support of the implant or implant breakage.

It is unfortunate that implant flexural stiffness increases at an exponential rate, typically at powers between two and four, depending upon implant geometry, relative to linear increases in implant dimension. Further aggravating the situation is the fact that there is little correlation between the size of the patient and the diameter of the intramedullary canal. That is, a small, relatively light person may have a femur with a large diameter canal and a much larger person may have a femur with a smaller diameter canal. Therefore, it has been considered desirable to produce an implant, especially a larger diameter implant, with greatly reduced stiffness in relation to its stem diameter.

This has been accomplished in several ways. For example, the use of materials which are inherently less stiff, that is, possess a lower flexural modulus, might be considered. Thus, the use of A material with a lower modulus of elasticity in lieu of the stiffer cobalt-chrome alloy might be considered. An implant can also be hollowed out. This method is marginally effective, however, due to the fact that the centrally located material contributes little to the stiffness of the implant. For example, if an implant with a round stem of 16 mm diameter is hollowed to a wall thickness of only 2 mm, the resulting decrease in flexural stiffness is only 32% while the decrease in mass is 56%. Interestingly, a 16 mm diameter stem is 6.5 times stiffer than the 10 mm diameter stem.

Morscher and Dick reported on nine years of clinical experience with a so-called "isoelastic" shaft prosthesis manufactured using polyacetal resin to transmit forces from the pelvis through the femoral head and neck into the femur in their paper: "Cementless Fixation of 'Isoelastic' Hip Endoprostheses Manufactured from Plastic Materials", *Clinical Orthopaedics*, June, 1983, Volume 176, pages 77–87. They stated: "The optimal fixation of an implant depends mainly on its design and material. The insertion of an artificial joint induces remodeling of the bony structures. If stability is not achieved, the implant sooner or later will loosen. The elasticity, and consequently the deformation, of an implant depends on the elastic modulus of the material and on the prosthetic design. By adjusting the physical characteristics of the foreign material to that of the bone tissue, as well as the design of the prosthesis to the femoral shaft, the entire system would have the same elasticity as a normal femur. A more elastic hip endoprosthesis also may act as a shock absorber during walking, particularly in the heel/strike and toe/off phases."

They proceeded to explain that this was the concept of the "isoelastic" hip endoprosthesis manufactured by Robert Mathys and implanted in 1973. In this instance, the prosthesis was composed of polyacetal resin which has an elasticity modulus approaching that of bone tissue, good durability, and tenacity for highly stressed components in combination with good tissue tolerance. To achieve the acquired structural strength in the neck portion, the component was reinforced by a metallic core that was radiused toward the tip to increase the elasticity of the stem, thereby allowing the stem of the prosthesis to follow the deformation of the bone. In commenting on the design, the authors further stated: "Isoelasticity implies the optimum approximation of the physical characteristics of an implant to those of the bone. An ideal isoelasticity, however, can never be achieved, since bone is anisotropic and the alloplastic materials used for joint arthroplasty snow isotropic properties. In addition, there is no adaptation of the structures to the forces acting on the hip, as in the case in viable bone. Moreover, the variety of individual forms and strengths of human bone can never be imitated by an artificial joint. Use of more elastic materials, however, should avoid the disadvantages of the rigid materials used to date."

U.S. Pat. No. 4,287,617 to Tornier discloses a hip prosthesis with a femoral stem which provides a measure of the elasticity spoken of by Morscner and Dick. A transverse section of the Tornier stem is in the form of a substantially rectangular tube of which one of the small sides is virtually cut away so as to leave a very large slot. The C-shaped section thus obtained is said to exhibit excellent transverse elasticity which facilitates the positioning of the pin in the medullary cavity by insertion. Other stated advantages are that the pin is not as heavy as solid designs, and that the cavity encourages bone growth.

An alternate approach to the foregoing is the subject of commonly assigned U.S. Pat. No. 4,808,186 to Todd S. Smith entitled "Controlled Stiffness Femoral Hip Implant". In that construction, the medial side of the length of the implant is milled out to form a channel shaped stem cross section. The amount of material removed determines the resulting decrease in stiffness of the implant while the outside geometry remains substantially unchanged with the exception of the open channel on the medial side of the implant. The resulting longitudinal channel lies generally in the coronal plane when the stem is in the implanted condition. The depth of the channel is variable between the proximal and distal ends of the femoral implant so as to affect the mass moment of inertia at any given location along a length of the stem to thereby achieve an optimal stem flexibility. That is, the stem is so formed that at specified locations along its length, it substantially correlates to the flexibility of the femur itself.

Yet another alternative approach to the foregoing is disclosed in U.S. Pat. No. 4,986,834 to Todd Smith et al., also commonly assigned, entitled "Load Sharing Femoral Hip Implant". Briefly stated, in that instance, the central portion of the length of a femoral implant is machined to reduce its outside dimension such that it has a smaller cross section. The amount of material removed determines the resulting decrease in stiffness of the implant. The reduced section of the implant may be variable between the proximal and distal ends of the femoral implant so as to affect the mass moment of inertia at any given location along a length of the stem to thereby achieve an optimal stem flexibility. In short, the stem is so formed that at specified locations along its length, it substantially correlates to the flexibility of the femur itself.

SUMMARY OF THE INVENTION

It was with knowledge of the foregoing that the present invention was conceived and has now been reduced to practice. According to the present invention, a femoral component of an artificial hip joint includes an elongated stem with a single longitudinally extending, generally medially facing, groove in its outer surface intermediate its proximal and distal ends. The dimensions of the groove are chosen so as to obtain a predetermined stiffness profile of the stem between the proximal and distal ends. In either event, the stem has a magnitude of stiffness no greater than that at which stress shielding of the first bone has been clinically identified by radiographic methods. The groove and the outer surface of the stem intersect at an outer rim. The groove has a central concave surface and proximal and distal radiused end surfaces in communication with and blending smoothly with the central cylindrical concave surface. The groove is disposed at an angle relative to the coronal plane, extending axially and can be angled either anteriorly or posteriorly to customize its stiffness. The component is preferably composed of cobalt-chromium alloy, but this principle is applicable to titanium or titanium alloy as well. The outer surface of the stem may be provided with a porous medium for encouraging bone ingrowth fixation.

By reducing the stiffness of a conventional femoral implant, more load is borne by the surrounding bone. This, in turn, will reduce bone mineral loss caused by stress shielding and promote the longevity of the hip arthroplasty.

The invention enables the reduction of the stiffness of a femoral hip implant in a controlled fashion. A controlled stiffness over a larger area, especially in the proximal or metaphyseal region of the implant, serves to provide a more uniform load distribution along the length of the femur.

The invention also maintains a controlled flexibility in the mid stem region while still affording extensive proximal and distal fixation. In contrast, prior art components only allowed mid stem or distal flexibility while adversely reducing the potential fixation area. By reason of the groove formed in the femoral stem of the invention, the neutral axis (bending axis) is shifted laterally thereby increasing flexibility while maintaining a clinically acceptable level of structural integrity and strength.

The femoral stem exhibiting the qualities of the invention may be composed of any of the common materials generally employed for implants. However, of these, titanium, titanium alloy, and cobalt chromium alloy would be preferable.

Other and further features, objects, advantages, and benefits of the invention will become apparent from the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention and, together with the description, serve to explain the principles of the invention in general terms. Like numerals refer to like parts throughout the disclosure.

BRIEF DESCRIPTION OF THE DRAWINGS

FIG. 3 is a side elevation view of the femoral component, certain parts being cut away and shown in section;

FIG. 4 is a top plan view of the femoral component;

DETAILED DESCRIPTION OF THE PREFERRED EMBODIMENT

Figure 1:
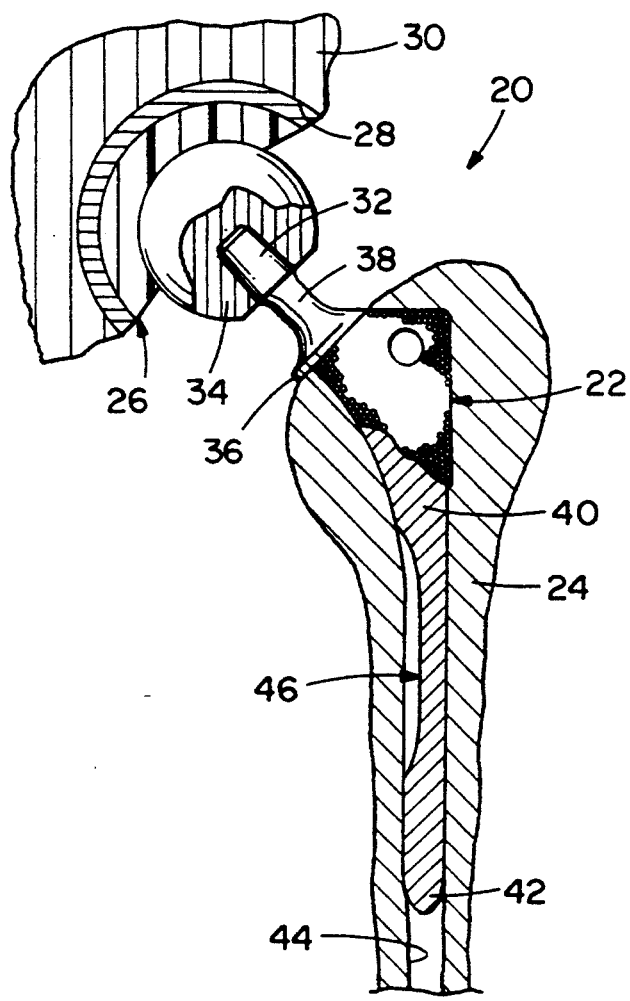
FIG. 1 is a side elevation view, certain parts being cut away and shown in section, of a hip prosthesis, including a femoral component embodying the invention.
Figure 2:
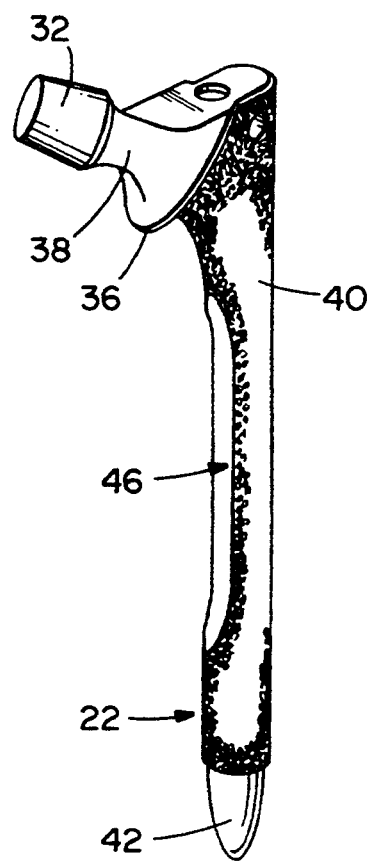
FIG. 2 is a perspective view of the femoral component of FIG. 1.

Turn now to the drawings, and initially to FIG. 1, which illustrates a hip prosthesis 20 including a femoral component 22 which embodies the invention. The femoral component 22, which may be of any material commonly used, such as a cobalt-chromium alloy, titanium, and titanium alloy, is suitably implanted in a femur 24 and is cooperatively engaged with an acetabular component 26. The latter component is suitably implanted in the acetabular cavity 28 of a pelvis 30. In customary fashion, the femoral component 22 has a taper 32 at its extreme proximal end (FIGS. 1–4) adapted to fittingly receive thereon a ball 34 (FIG. 1). In turn, the ball is rotatably engaged with the acetabular component 26 in a known manner. The femoral component further includes a collar 36, with the taper 32 being joined to the shoulder via a next 38. A stem 40 extends away from the collar 36 to a distal or tip end 42.

Figure 5:
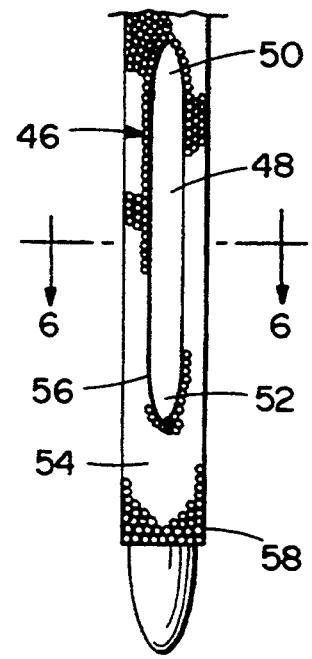
FIG. 5 is a detail front elevation view of a portion of the femoral component.
Figure 6:
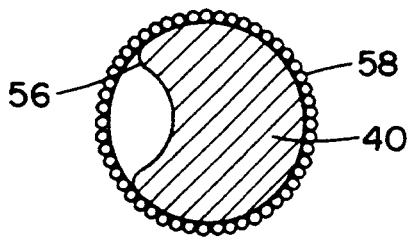
FIG. 6 is a cross section view taken generally along line 6—6 in FIG. 5.

In a customary manner, the stem 40 is received in the intramedullary canal 44 (FIG. 1) of the femur and lies generally in the coronal plane of the body of the person in whom the prosthesis is implanted. The lateral dimensions of the stem (see especially FIG. 2) are substantially constant between the collar 36 at the proximal end and the distal end 42 of the femoral component 22. The stem is formed in any suitable manner with a single longitudinally extending groove 46 intermediate in its proximal and distal ends. As best seen in FIGS. 3 and 5, the groove 46 includes a central concave surface 48 of substantially constant curvature as the stem is viewed in cross section (FIG. 6) and proximal and distal radiused end surfaces 50, 52, respectively. The central concave surface and the radiused end surfaces 50, 52 intersect with an outer surface 54 of the stem, the intersection occurring at an outer rim 56. The radiused end surfaces blend smoothly with the central concave surface 48 to prevent the occurrence of any undue stress concentrations.

It may be desirable to modify the stem to have a porous surface 58 enabling bone ingrowth fixation. An excellent example of such a surface results from application of the proprietary porous metal coating of DePuy[R] Division of Boehringer Mannheim Corporation provided under the trademark "POROCOAT". The porous surface 58 may be applied to specified portions of the outer surface 54.

The shape and dimensions of the groove 46 are chosen so as to obtain substantially controlled stiffness of the stem 40 between its proximal and distal ends. Its purpose is to affect the mass moment of inertia of the femoral component at any given location along the length of the stem to thereby achieve a controlled stem flexibility. The shape of the cross section of the stem need not be circular but may include asymmetrical shapes, as desired, so long as substantially constant stem flexibility is maintained. The goal sought to be achieved by the stem 40 is that at all locations along its length it exhibits a magnitude of stiffness no greater than that at which stress shielding of the bone 24 would occur.

For proper angular placement of the groove, the anatomic loading on the femoral component is determined, then the longitudinal axis of the groove is placed in the plane in which loading occurs.

The groove 46 has a longitudinal axis parallel to the longitudinal axis of the stem and lies within a central bisecting plane which is generally angularly disposed relative to the coronal plane when the stem is implanted. The central bisecting plane of the longitudinally extending groove may be disposed at an angle within a range of 0° to approximately 45° relative to the coronal plane and extends axially, although a range of 0° to approximately 18° is preferred. The groove can be angled either anteriorly or posteriorly to customize its stiffness.

It was previously mentioned that implant flexural stiffness increases at an exponential rate, typically at powers between two and four, depending upon implant geometry, relative to linear increases in implant dimension. Graphic proof of this statement is presented in FIG. 7 which is a bar graph indicating relative stiffness of a series of stems of varying diameters which are currently available for implanting. It is noteworthy that the 18 millimeter diameter stem exhibits approximately 10 times the stiffness of the 10.5 millimeter diameter stem. The invention serves to avoid this exponential increase. For example, as seen from the graph in FIG. 7, beginning with the 13.5 millimeter stem, if a 13.5 mm diameter stem was determined as the adoptive remodeling threshold, it would be desirable to maintain that stiffness on implants 13.5 mm diameter and above.

Figure 7:
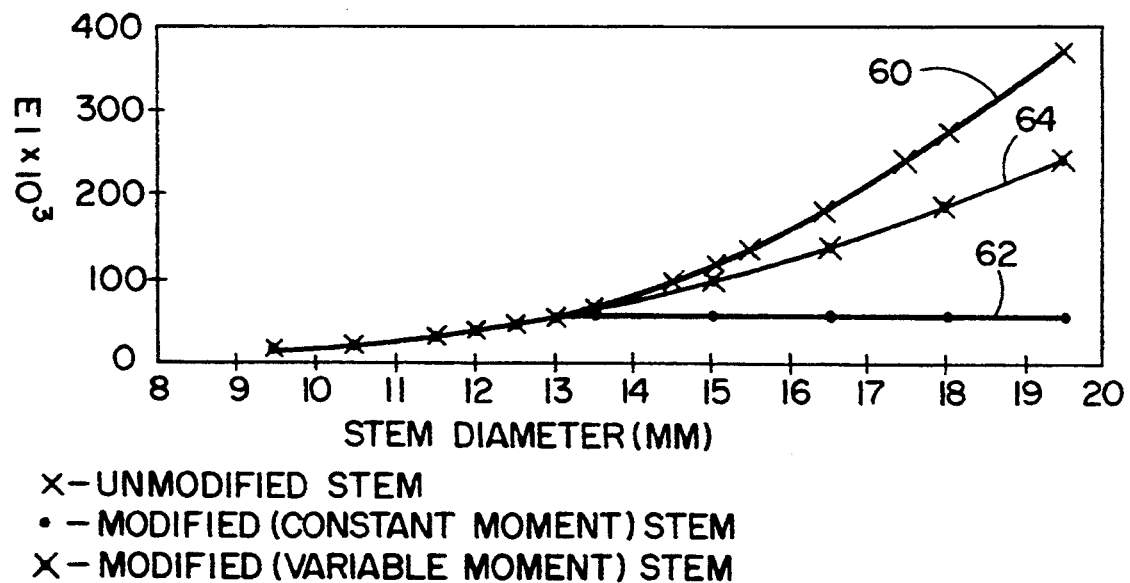
FIG. 7 is a bar graph indicating relative stiffness of a series of stems of varying diameters for femoral components which are currently available commercially, as well as stems embodying the teachings of the present invention.

It will also be noted on the graph of FIG. 7 that data is indicated relating to another modified stem, this one being a variable moment stem. In this instance, the groove 46 is so designed that the stem does not exhibit constant stiffness across the range of stem sizes, but rather increasing stiffness at a lesser rate than the unmodified stem. In theory, a surgeon could have available to him a range of femoral components from which he could choose should he desire one with a specific stiffness profile.

Figure 8:
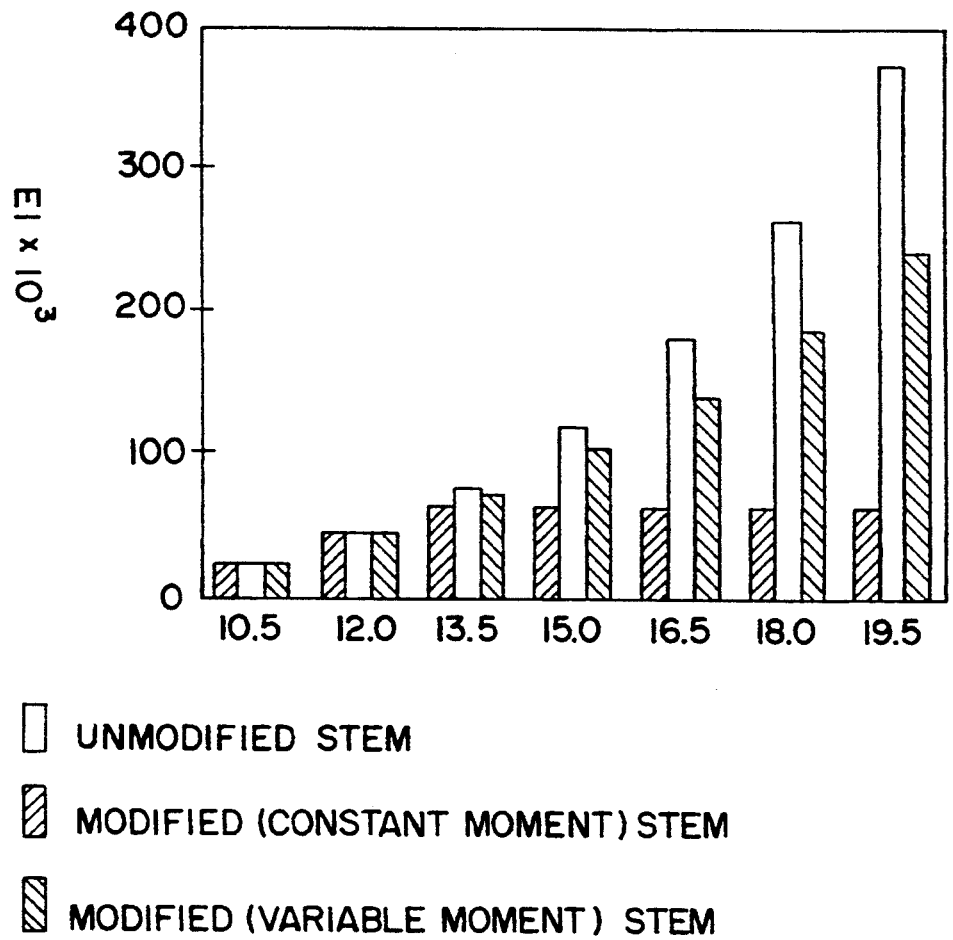
FIG. 8 is a line graph generally depicting the information presented in FIG. 7.

FIG. 8 is a line graph generally presenting the information of FIG. 7 in a different format. In this instance, curve 60 represents the unmodified stem, curve 62 represents the modified, constant moment, stem, and curve 64 represents the modified, variable moment, stem.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A component of an artificial joint for replacing a damaged natural joint in a skeletal structure of a body which includes a prosthesis having a first cooperating member to be secured to a first long bone having an intramedullary canal, the first cooperating member adapted to engage and being relatively movable with a second cooperating member of a second bone to permit relative movement between the first and second bones, comprising:

an elongated stem having an outer surface and a longitudinal axis lying generally in a coronal plane and being integral with the first cooperating member and receivable in the intramedullary canal of the first bone, said stem extending between proximal and distal ends and having a single longitudinally extending, generally medially facing, groove intermediate said proximal and distal ends, said groove and said outer surface intersecting at a single outer rim, said groove including a central concave surface and proximal and distal concave end surfaces, said groove having a longitudinal axis parallel to said longitudinal axis of said stem lying within a central bisecting plane which is generally angularly disposed relative to the coronal plane when said stem is implanted, said central bisecting plane of said longitudinally extending groove being disposed at an angle within a range of 0° to approximately 45° relative to the coronal plane and extending in a lateral posterior to medial anterior direction, said proximal and distal end surfaces extending to said rim and blending smoothly with said central concave surface, said groove having a substantially constant depth between said proximal and distal concave end surfaces chosen so as to obtain a substantially constant stiffness profile of said stem between said proximal and distal ends such that said stem with said groove therein at all locations between said proximal and distal ends has a magnitude of stiffness no greater than a predetermined magnitude corresponding to that at which stress shielding of the first bone would occur.

2. A component as set forth in claim 1 which is composed of any one of titanium, titanium alloy, and cobalt-chromium alloy.

3. A component as set forth in claim 1 wherein said outer surface of said elongated stem has a porous medium thereon for encouraging bone ingrowth fixation.

4. A component of an artificial joint for replacing a damaged natural joint in a skeletal structure of a body which includes a prosthesis having a first cooperating member to be secured to a first long bone having an intramedullary canal, the first cooperating member adapted to engage and being relatively movable with a second cooperating member of a second bone to permit relative movement between the first and second bones, comprising:

an elongated stem having an outer surface and a longitudinal axis lying generally in a coronal plane and being integral with the first cooperating member and receivable in the intramedullary canal of the first bone, said stem extending between proximal and distal ends and having a single longitudinally extending groove intermediate said proximal and distal ends, said groove and said outer surface intersecting at a single outer rim, said groove including a central concave surface and proximal and distal concave end surfaces, said groove having a longitudinal axis parallel to said longitudinal axis of said stem lying within a central bisecting plane which is generally angularly disposed relative to the coronal plane when said stem is implanted, said central bisecting plane of said longitudinally extending groove being disposed at an angle within a range of 0° to approximately 45° relative to the coronal plane and is angled either anteriorly or posteriorly to accommodate the anatomy of the recipient, said proximal and distal end surfaces extending to said rim and blending smoothly with said central concave surface, said groove having a substantially constant depth between said proximal end and distal concave end surfaces chosen so as to obtain a substantially constant stiffness of said stem between said proximal and distal ends such that said stem with said groove therein at all locations between said proximal and distal ends has a magnitude of stiffness no greater than a predetermined magnitude corresponding to that at which stress shielding of the first bone would occur.

5. An artificial joint as set forth in claim 4 which is composed of any one of titanium, titanium alloy, and cobalt-chromium alloy.

6. A component as set forth in claim 4 wherein said outer surface of said elongated stem has a porous medium thereon for encouraging bone ingrowth fixation.

7. An artificial joint for replacing a damaged natural hip joint in a skeletal structure of a body comprising:

a cup shaped socket member fixed to the pelvis of the body;

a ball member rotatably engageable with said socket member;

an elongated stem having an outer surface and a longitudinal axis lying generally in a coronal plane and being integral with said ball member and receivable in the intramedullary canal of the femur of the body, said stem extending between proximal and distal ends and having a single longitudinally extending groove intermediate said proximal and distal ends, said groove and said outer surface intersecting at a single outer rim, said groove including a central concave surface and proximal and distal concave end surfaces, said groove having a longitudinal axis parallel to said longitudinal axis of said stem lying within a central bisecting plane which is generally angularly disposed relative to the coronal plane when said stem is implanted, said central bisecting plane of said longitudinally extending groove being disposed at an angle within a range of 0° to approximately 18° relative to the coronal plane and extending in a lateral posterior to medial anterior direction, said proximal and distal end surfaces extending to said rim and blending smoothly with said central concave surface, said groove having a substantially constant depth between said proximal and distal concave end surfaces chosen so as to obtain a substantially constant stiffness profile of said stem between said proximal and distal ends such that said stem with said groove therein at all locations between said proximal and distal ends has a magnitude of stiffness no greater than a predetermined magnitude corresponding to that at which stress shielding of the first bone would occur.

8. A component as set forth in claim 7 which is composed of any one of titanium, titanium alloy, and cobalt-chromium alloy.

9. A component as set forth in claim 7 wherein said outer surface of said elongated stem, excluding said longitudinally extending groove, has a porous medium thereon for encouraging bone ingrowth fixation.

* * * * *